(12) United States Patent
Carter et al.

(10) Patent No.: US 8,362,176 B2
(45) Date of Patent: Jan. 29, 2013

(54) METHOD OF MAKING TRIGLYCERIDE MACROMONOMERS

(75) Inventors: Jeff T. Carter, Middlesborough (GB); Steve Quinn, Darlington (GB)

(73) Assignee: Akzo Nobel Coatings International B.V., Arnhem (NL)

( * ) Notice: Subject to any disclaimer, the term of this patent is extended or adjusted under 35 U.S.C. 154(b) by 163 days.

(21) Appl. No.: 12/808,999

(22) PCT Filed: Dec. 16, 2008

(86) PCT No.: PCT/EP2008/067579
§ 371 (c)(1),
(2), (4) Date: Jul. 15, 2010

(87) PCT Pub. No.: WO2009/080599
PCT Pub. Date: Jul. 2, 2009

(65) Prior Publication Data
US 2010/0298464 A1    Nov. 25, 2010

(30) Foreign Application Priority Data
Dec. 19, 2007  (GB) .................................. 0724720.8

(51) Int. Cl.
*C08F 22/10* (2006.01)
*C07C 51/353* (2006.01)

(52) U.S. Cl. ......... 526/321; 524/556; 524/559; 554/126
(58) Field of Classification Search ................. 554/126; 524/556, 559; 526/321
See application file for complete search history.

(56) References Cited

U.S. PATENT DOCUMENTS

| | | | |
|---|---|---|---|
| 5,719,301 A | 2/1998 | Sleeter | |
| 6,121,398 A | 9/2000 | Wool et al. | |
| 6,646,085 B1 | 11/2003 | Craun et al. | |
| 2005/0203246 A1 | 9/2005 | Thames et al. | |

FOREIGN PATENT DOCUMENTS

| | | |
|---|---|---|
| DE | 3938149 A1 | 5/1991 |
| WO | WO 99/21900 A | 5/1999 |

(Continued)

OTHER PUBLICATIONS

English Abstract of DE 3938149 A1 (May 23, 1991).*

(Continued)

*Primary Examiner* — Vu A. Nguyen
(74) *Attorney, Agent, or Firm* — Kenyon & Kenyon LLP (57) ABSTRACT

A process of making a polymerisable ethylenically unsaturated macromonomer from an unsaturated non-mineral oil, the oil being a mixture of triglycerides, some of which comprise at least one fatty acid having at least two non-conjugated unsaturated bonds at least one of which is ethylenically unsaturated, the process comprising the steps of: i) conjugating the non-conjugated unsaturated bonds, ii) reacting the reaction product of step (i) with an enophile having an acid, ester or anhydride moiety to form an adduct, iii) reacting the adduct with an ethylencially unsaturated monomer having a moiety reactive with the acid, ester or anhydride moiety of the enophile to form an intermediate iv) reacting the intermediate of step (iii) with a chain extender having at least two moieties reactive with the acid, ester or anhydride moiety of the enophile to form the macromonomer, where the oil has an iodine value of from 110 to 180 g of iodine per 100 g of oil.

20 Claims, 2 Drawing Sheets

FOREIGN PATENT DOCUMENTS

WO  WO 2005071050 A1 * 8/2005

OTHER PUBLICATIONS

Soybean oils—Wikipedia (Feb. 23, 2012).*
International Search Report, PCT/EP2008/067579, mailed Apr. 29, 2009, 3 pages.
Written Opinion of International Searching Authority, PCT/EP2008/067579, mailed Apr. 29, 2009, 6 pages.
Reply to Written Opinion of International Searching Authority, PCT/EP2008/067579, dated Sep. 30, 2009, 3 pages.
International Preliminary Report on Patentability, PCT/EP2008/067579, completed on Mar. 29, 2010.
International Search Report, PCT/EP2008/067578, mailed Apr. 21, 2009, 3 pages.
Gultekin, M. et al., "Styrenation of castor oil and linseed oil by macromer method," Macromol. Mater. Eng., vol. 283, 2000, pp. 15-20 (XP002522953).
International Search Report, PCT/EP2008/067577, mailed Apr. 24, 2009, 2 pages.

* cited by examiner

Figure 1

Figure 2

METHOD OF MAKING TRIGLYCERIDE MACROMONOMERS

REFERENCE TO RELATED APPLICATIONS

This application is the U.S. National Phase of PCT/EP2008/067579 filed on Dec. 16, 2008, and claims the benefit of GB Application No. 0724720.8, filed on Dec. 19, 2007.

This invention relates to a process of making ethylenically unsaturated macromonomers derived from conjugated unsaturated non-mineral oils-especially plant and vegetable oils; polymers-particularly in the form of aqueous dispersions derived from them and finally adhesives, coatings, especially architectural coatings, comprising the polymers.

By architectural coatings is meant paints, varnishes and woodstains, especially for use on the interior and exterior of structures and buildings such as houses, and also coatings for use in the garden such as fence paints and also metal used on railings.

There is increasing awareness of the need to use renewable resources in industry.

For many years, the main feedstock for industry, especially the chemical industry, has been fossil feedstock, either in the form of petroleum or coal. Whilst economists, mining and oil exploration experts may argue about the lifetime of known and yet to be discovered fossil feedstock reserves, it is indisputable that, in time, those reserves will inevitably be exhausted and even prior to that, become too expensive to be of any use as a feedstock in all but the most specialised applications.

Furthermore, converting this fossil feedstock into useful material for industry requires energy, releasing carbon dioxide and contributing to global warming. In addition, at the end of the useful life of the material, still more carbon dioxide is released, further adding to global warming.

Coatings typically comprise a mixture of particulate inorganic material and organic material. The inorganic material is usually a mixture of pigments and fillers and/or extenders. The pigments give colour to the paint and the fillers and extenders provide other properties, such as hardness, to the paint film. The organic material largely comprises a binder, the role of which, as the name suggests, is to bind any particulate matter together. It also provides adhesion to the surface to which the coating is applied.

The binders are usually high molecular weight polymers derived from monomers obtained by refining and further processing of fossil feedstock. The polymers are often produced in the form of aqueous dispersions of polymer microparticles referred to as latex. For simplicity it should be understood that the term polymer is used here to include homopolymers, copolymers, terpolymers and so on.

The manufacture and use of such polymer binders consumes some of the worlds non-renewable resources and in the process produces carbon dioxide.

Thus there is a need for polymer binders that are based, at least in part, on renewable feedstock such as that obtained from plant and/or animal material.

Oils are such a natural and renewable feedstock obtainable from various plants and animals, including fish. In the case of plants, it is generally the fruit that yields the oil. The term oil as used here, excludes mineral oils obtained form fossil feedstock such as petroleum and coal.

These oils are largely composed of a mixture of triglycerides (ie tri-esters of glycerol) characterised by the fatty acids portion. For example, the fatty acids component of the triglycerides making up palm oil, linseed oil and soya oil are shown below and have the following approximate composition by weight %:

| | | Palm oil | Linseed oil | Soya oil |
|---|---|---|---|---|
| Palmitic acid | ($C_{16}$, 0) | 44 | 6 | 10 |
| Stearic acid | ($C_{18}$, 0) | 4.5 | 2.5 | 4 |
| Arachidic | ($C_{20}$, 0) | 0 | 0.5 | 0 |
| Oleic acid | ($C_{18}$, 1) | 40 | 19 | 23 |
| Linoleic | ($C_{18}$, 2) | 10 | 24.1 | 51 |
| Linolenic | ($C_{18}$, 3) | 0 | 47.4 | 7 |
| Other | | 1.5 | 0.5 | 5 |
| Saturated | | 48.5 | 9 | 14 |
| Unsaturated (total) | | 50.0 | 90.5 | 81 |
| Unsaturated (>1) | | 10.0 | 71.5 | 58 |
| Iodine value | | 44-54 | 155-205 | 120-141 |

The subscript refers to the carbon chain length of the fatty acid and 0, 1 or 2 indicates the number of ethylenically unsaturated bonds in the fatty acid.

Such unsaturated oils can be classified as drying, non-drying or semi-drying oils. What is meant by such terminology is the extent to which they autoxidise at normal temperatures to form a hard, dry film. Autoxidation is the process by which unsaturated oils absorb oxygen from the atmosphere to form in-situ hydroperoxides which then decompose to produce free radicals causing the oils to dry. The more unsaturated bonds the oil has, the more rapidly and completely it will dry. Similarly, oils with at least two unsaturated bonds per triglyceride, especially when conjugated, autoxidise even more readily. However, oils having such conjugation tend to have a yellow colour which intensifies on drying.

The extent of the unsaturation is measured by the iodine value. It is generally regarded that non-drying oils have iodine values of less than 100, semi-drying oils from 100 to 140 and drying oils over 140 g of iodine per 100 g of oil. A more extensive list of iodine values can be found on pages 34 and 35 of The Chemistry of Organic Film Formers by D. H. Solomon, published by John Wiley and Sons in 1967, which are hereby incorporated by reference. The oils can be characterised according to the number of double bonds per triglyceride type. We have found that a typical sample of palm oil, for example, has the following distribution, expressed on a weight % basis.

| | |
|---|---|
| 5 double bonds per triglyceride | <1 |
| 4 double bonds per triglyceride | ca 10 |
| 3 double bonds per triglyceride | ca 5 to 10 |
| 2 double bonds per triglyceride | ca 35 |
| 1 double bonds per triglyceride | ca 35 to 40 |
| 0 double bonds per triglyceride | ca 10 |

Thus whilst approximately 48.5% of the fatty acids in the oil are palmitic or stearic and thus saturated, nevertheless only about 10% of the triglycerides will be composed of fatty acids where all three are saturated, and therefore free of double bonds. This saturated portion of the palm oil is unreactive to enophile and dienophiles.

In our co-pending European patent application EP 07024602 we show how to make an ethylencially unsaturated macromonomer starting from unsaturated non-mineral oils of the type mentioned above. The macromonomer is the product of i) an adduct formed from the reaction of an unsaturated non-mineral oil reacted with an enophile having an acid, ester or anhydride moiety and ii) an ethylenically unsaturated monomer having a moiety reactive with the acid, ester or anhydride moiety of the enophile and iii) a chain extender material having at least two moieties reactive with the acid, ester or anhydride moiety of the enophile.

This produces macromonomers which can be polymerised with other monomers to form a variety of polymers suitable for use in many applications, including binder polymers for use in coatings. However, such polymers tend to have a slight yellow colour which increases in intensity as the film ages and/or is stored in the dark.

In the field of architectural coatings, especially the popular pastel shades, such yellowing in the binder is evident in the dried coating and detracts from the decorative effect intended, especially over time. Clearly, consumers do not like this.

Thus there is a need to reduce both the initial yellow colour of binders made from such oil based macromonomers and their colour after aging, in particular, at elevated temperature and/or in the dark.

We have now found that yellowing in binders derived from such macromonomers can be reduced by conjugating any unsaturated bonds present in the triglycerides comprising the oil, prior to the reaction with the enophile.

According to the present invention there is provided a process of making a polymerisable ethylenically unsaturated macromonomer from unsaturated non-mineral oil, the oil being a mixture of triglycerides, some of which comprise at least one fatty acid having at least two non-conjugated unsaturated bonds at least one of which is ethylenically unsaturated, the process comprising the steps of i) conjugating the non-conjugated unsaturated bonds ii) reacting the reaction product of step i) with an enophile having an acid, ester or anhydride moiety to form an adduct iii) reacting the adduct with an ethylencially unsaturated monomer having a moiety reactive with the acid, ester or anhydride moiety of the enophile to form an intermediate iv) reacting the intermediate of step iii) with a chain extender having at least two moieties reactive with the acid, ester or anhydride moiety of the enophile to form the macromonomer where the oil has an iodine value of from 110 to 180 g of iodine per 100 g of oil.

Preferably the conjugation of step i) is carried out by reacting the oil with from 0.1 to 0.8 wt % of iodine, calculated on the weight of oil. More preferably, step i) is carried out at a temperature of between 125 and 270° C.

The macromonomer is considered to be polymerisable through the ethylenic unsaturation provided by the monomer of step iii) rather than through any unreacted unsaturation in the fatty acid chains of the triglycerides comprising the oil. Normally, the polymerisable ethylenic unsaturation of the macromonomer is dependent from the fatty acid chain, usually indirectly, rather than exists in the backbone of the chain.

It is essential that step i) is performed before the oil is reacted with the enophile in order to conjugate the non-conjugated unsaturated bonds. By conjugating any suitable unsaturated bonds, the reaction of the oil with the enophile of step ii) ensures that the Diels-Alder reaction is favoured over the Alder-ene reaction. Surprisingly, it appears that by minimising the Alder-ene reaction results in reduced yellowing.

The term conjugation is here used to indicate at least two unsaturated bonds separated by one single bond. Non-conjugation is where the unsaturated bonds are separated by more than one single bond. In each case the bonds are between carbon atoms.

By unsaturated bonds we mean double or triple carbon-carbon bonds. Double bonds are also referred to as ethylenically unsaturated bonds.

Preferably the at least two unsaturated bonds are double bonds as this reduces the tendency to yellow.

Preferably, the amount of iodine used is from 0.20 to 0.80%, more preferably from 0.35 to 0.80%, even more preferably from 0.40 to 0.75% and most preferably from 0.50 to 0.70% calculated on the weight of the oil.

At levels below 0.1 wt % very little if any conjugation occurs and the reaction is slow. Above 0.8 wt % the iodine itself appears to give colour to the oil and is thus avoided.

Oils, or mixtures of oils, having iodine value less than 110 are thought to have insufficient unconjugated unsaturation to be useful in the invention, whilst those oils of iodine value greater than 180 are intensely coloured and thus not useful in this invention. Suitable oils include Soya bean oil, Sunflower oil, Safflower oil, Corn oil, Cottonseed oil, Flaxseed oil, Grape seed oil, Peanut oil, Sesame oil, Walnut oil.

Preferably the temperature of the reaction of iodine with the oil is from 150 to 250° C., more preferably from 170 to 250° C. and most preferably from 200 to 250° C. as these produce binders with low initial yellow colour and also yellow less when cast as films and stored in the dark or elevated temperatures.

Preferably the weight average molecular weight, Mw, of the macromonomer is 1000 to 50000 Daltons, more preferably from 1500 to 40000, still more preferably from 2000 to 40000, yet more preferably from 5000 to 30000 Daltons, even more preferably from 10000 to 25000 Daltons and most preferably form 19000 to 23000 Daltons. The number average molecular, Mn is preferably from 1000 to 5000 Daltons, more preferably from 1000 to 4000, even more preferably from 1000 to 3000 and most preferably from 1500 to 3000 Daltons.

For simplicity, the term enophile is used to include dienophile.

Enophiles have electron withdrawing moieties, such as ester, acid, cyanide and anhydride. Preferably the enophile is an electrophillic alkene or alkyne. Even more preferably is selected from the group consisting of maleic anhydride, fumaric acid, itaconic anhydride, acrylic acid and maleate esters and most preferably it is selected from the group consisting of maleic anhydride and fumaric acid.

By non-mineral oil is meant oil, comprising triglycerides, that has been obtained directly from plant or animal matter, including fish, rather than from a fossil feedstock.

Preferably, at least 80% by weight of the total triglycerides making up the oil contain one or more double bonds, more preferably 85 to 100%, still more preferably 90 to 100%, yet more preferably 95 to 100% and most preferably 100%. The amount of fully saturated triglycerides is preferably kept as low as possible as such triglycerides are unreactive to the enophile. The oily exudate seen on the surface of dried latex and paint films is thought to be this unreacted saturated material.

Being natural products, the composition of the oils varies significantly from year to year, the geographic location of the source and the degree of any further processing that may be carried out on the oil. Blending oils from different sources and even of different types not only produce a more consistent feedstock, but also enables oils having a triglyceride composition not found in nature to be produced.

However, even such blends are not ideal, because they consist of a complex mixture of triglycerides having saturated and mono and poly-unsaturated fatty acid portions. This inevitably results in a distribution of species being formed when the oils are subsequently reacted with polyfunctional material. There is also a risk of gelation.

Transesterification of oils, whereby the fatty acid portions between and within triglycerides are rearranged, can produce oils which, whilst not composed of the ideal triglyceride structure described above, nevertheless have more of the triglycerides with fewer unsaturated bonds, than the naturally occurring oil.

Transesterification can be carried out with a single oil, resulting in randomisation of the fatty acid composition of the triglycerides. Or it may be performed with a mixture, comprising two or more oils. Careful choice of the oil mixture to be interesterified allows the triglyceride composition to be controlled.

An additional benefit of transesterification is that by blending oils and transesterifying the resulting mixture, a more consistent feedstock can be produced for further reaction according to the invention.

Optionally, the macromonomer is diluted with a suitable solvent, preferably one that is also a polymerisable monomer in a final step. This ensures that the macromonomer does not solidify on cooling down from the reaction temperature and thereby become difficult to handle. 2-ethyl hexyl acrylate is a suitable such solvent/monomer. Other suitable such monomers include butyl acrylate and styrene.

Plant oils are preferred as their production consumes carbon dioxide rather than producing it.

All vegetable oils are a complex mixture of species. Nevertheless, average molecular weights are generally quoted in the region of 800 to 900 Daltons. Palm oil, for example has a molecular weight of 848 Daltons.

Preferably, the moiety on the ethylenically unsaturated monomer, reactive with the acid, ester or anhydride moiety of the enophile is a hydroxyl, amino or epoxide. Even more preferably, there is only one such moiety on the monomer.

Preferably the ethylenically unsaturated monomer reactive with the acid, ester or anhydride moiety of the enophile is selected from the group comprising hydroxyethyl (meth) acrylate, hydroxyl propyl (meth)acrylate, hydroxyl iso propyl methacrylate, hydroxyl butyl methacrylate, allyl alcohol, glycerol methacrylate, glycidyl (meth)acrylate, allyl amine, tert-butyl aminoethyl methacrylate. More preferred are hydroxy ethyl acrylate and hydroxyl ethyl methacrylate and most preferred is hydroxyl ethyl methacrylate.

The reaction of the ethylencially unsaturated monomer (step iii of the invention) is preferably carried out in the presence of a polymerisation inhibitor in order to prevent the monomer from homopolymerising. A suitable such inhibitor is phenothiazine.

Preferably the chain extender material comprises hydroxyl, amine, oxirane or isocyanate moieties. More preferably, it comprises at least two moieties capable of reacting with the acid, ester or anhydride moiety of the enophile. Nevertheless, it is possible that a trifunctional material is acceptable if one of the moieties is much slower to react than the other two. For example, this is thought to be the case when glycerol is used, where the secondary hydroxyl group is less reactive than the two primary hydroxyl groups. Preferably, the chain extender material is glycerol as it is readily obtained from sustainable plant material.

The mole ratio of oil:enophile is preferably less than or equal to 1, more preferably from 0.50 to 1.00, even more preferably from 0.55 to 0.75 and most preferably from 0.60 to 0.70.

The mole ratio of oil:chain extender is preferably greater than 1.8, more preferably from 1.8 to 10.0, even more preferably from 2.0 to 7.5, still more preferably from 2.5 to 5 and most preferably from 3.0 to 3.5.

The mole ratio of unsaturated monomer:oil is preferably less than 1:1, more preferably it is between 0.25:1 and 1:1, even more preferably from 0.3:1 to 0.9:1, yet more preferably from 0.5:1 and 0.85:1 and most preferably from 0.6:1 to 0.85:1. At these ratios, polymer films derived from such macromonomers tend to be harder than films derived from macromonomers of higher unsaturated monomer content. Furthermore, the reduced level of unsaturated monomer relative to the oil results in an increased content of renewable resource in the macromonomer and, thus, the final coating, which is environmentally beneficial. Finally, due to the high energy content required to produce the ethylenically unsaturated monomer, a significant cost saving is also realised.

The mole ratio of oil:enophile:unsaturated monomer:chain extender is preferably 1.00:1.50:0.75:0.30. Even more preferably the oil is Soya bean oil, the enophile is maleic anhydride, the unsaturated monomer is hydroxyl ethyl (meth) acrylate—most preferably hydroxyl ethyl methacrylate, and the chain extender is glycerol.

The reaction of the oil with the enophile is thought to produce an adduct of the triglycerides comprising the oil, and the enophile. The adduct having an acid, ester or anhydride moiety reacts with a suitable functional moiety on the ethylenically unsaturated monomer to form an intermediate polymerisable triglyceride monomer. Further reaction with a chain extender material, increases the molecular weight of the intermediate thereby ensuring that the proportion of triglyceride not functionalised with the unsaturated monomer of step iii) is kept to a minimum. This reduces the tendency for exudation from polymers comprising such monomers.

Preferably, the molecular weight of the resulting macromonomer of the invention is at least twice that of the reaction product of step iii).

As the macromonomer is the product of an oil comprising a mixture of triglycerides, some of which have a functionality greater than one, with other reactants also having functionality greater than one, the macromonomer is thought to be a complex mixture of species.

In practice, the reaction of the triglycerides with the enophile to form the adduct is further complicated because the triglycerides (of the oil) themselves can have differing degrees of unsaturation (ie mono-, di- or tri-ene).

Figure 1:
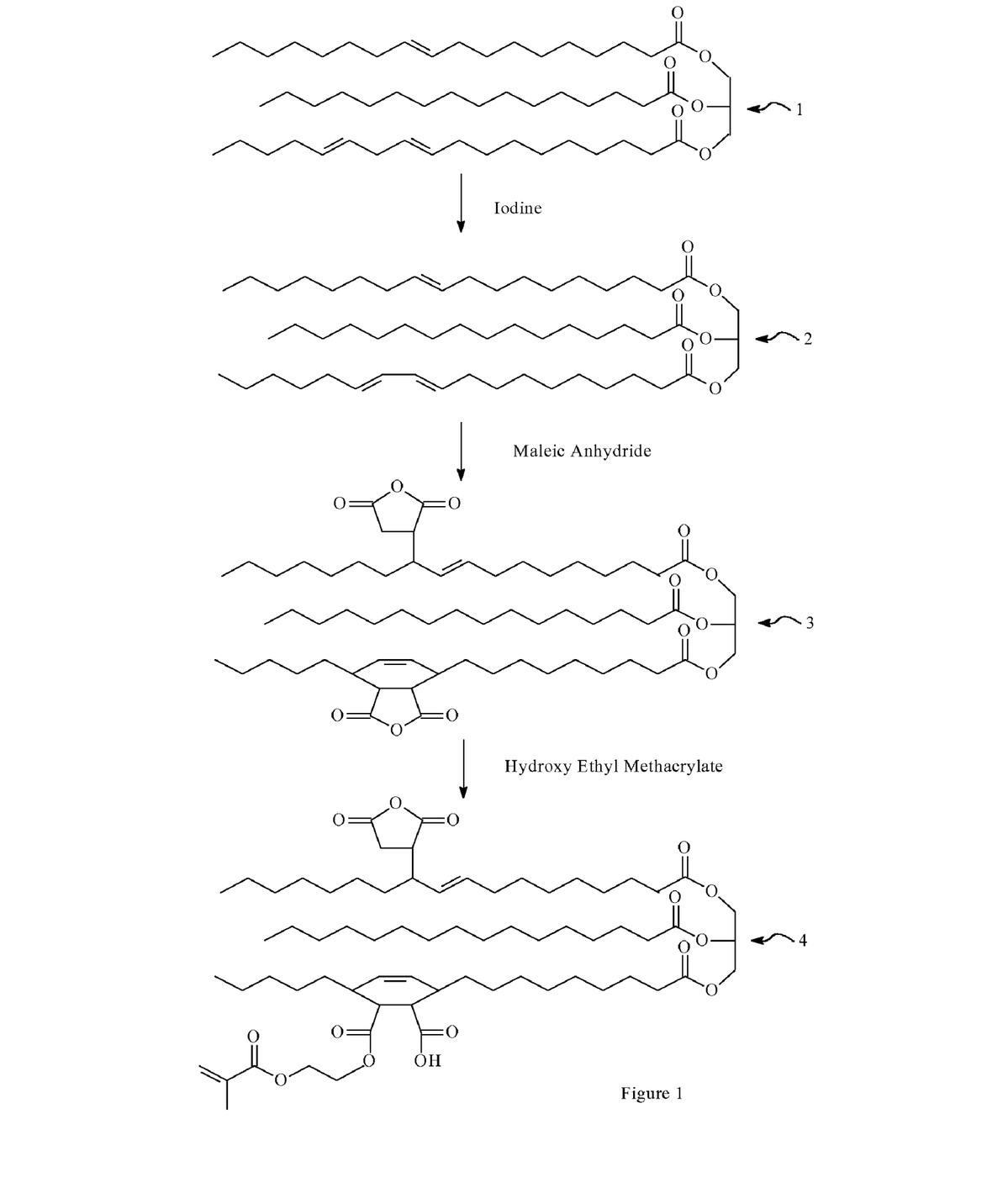
Figure 2:
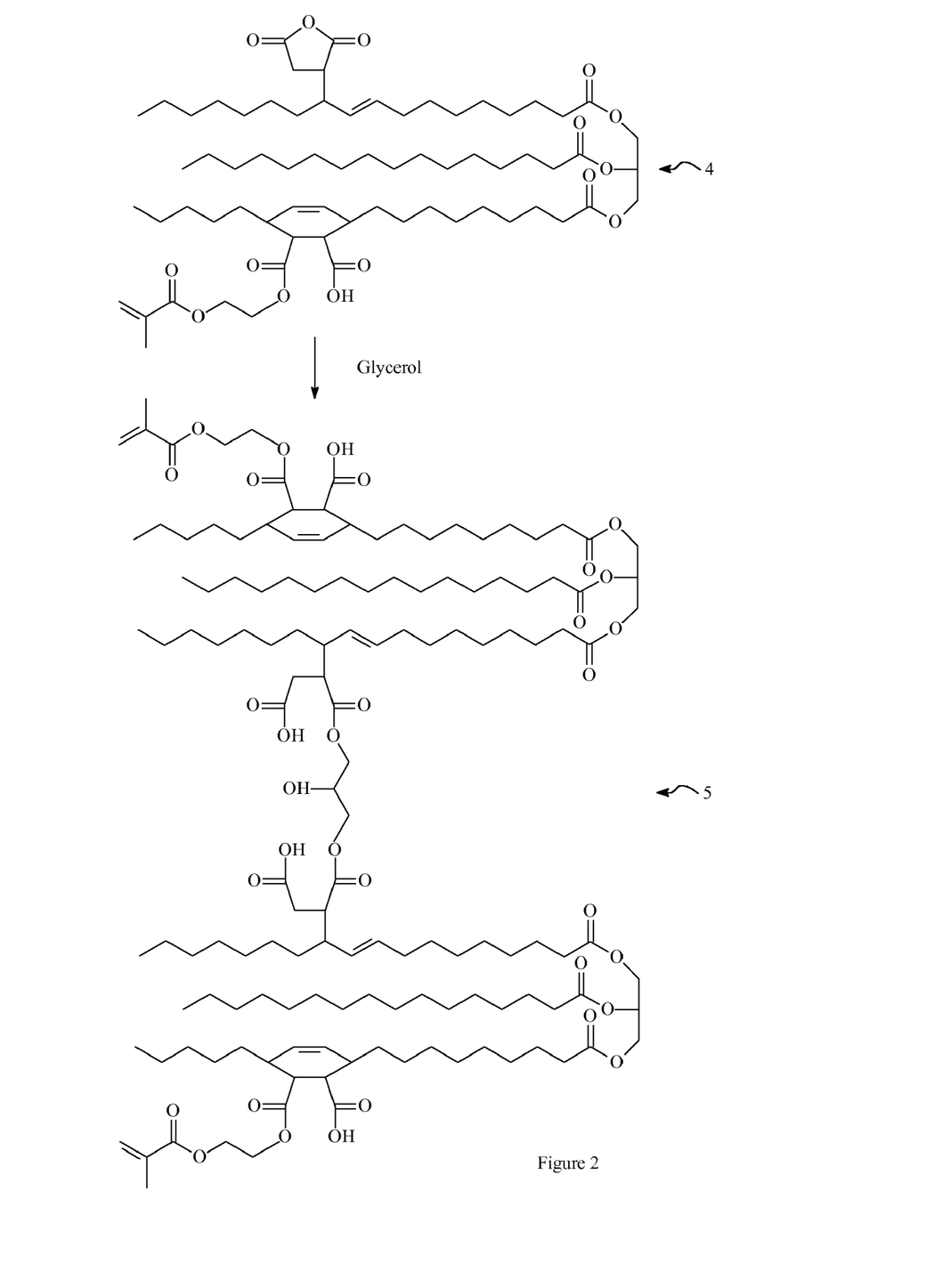

FIGS. 1 and 2 show a simplified and idealised diagrammatic scheme for the formation of one of the species that make up the macromonomer of the invention. In this case the enophile is maleic anhydride; the unsaturated monomer is hydroxyl ethyl methacrylate and the chain extender is glycerol.

FIG. 1 shows a reaction scheme of a triglyceride (1) reacting with maleic anhydride and hydroxyl ethyl methacrylate. The triglyceride comprises a saturated fatty acid-palmitic acid, a mono-unsaturated fatty acid-oleic acid and an unconjugated diene fatty acid-linoleic acid. In the presence of sufficient iodine in accordance with the present invention, any unconjugated diene becomes conjugated as shown in structure (2). This troglyceride comprising a conjugated diene fatty acid reacts with the maleic anhydride via the Diels-Alder reaction to form the adduct containing the cyclic hexene structure depicted as (3). Furthermore, in some circumstances any any non-conjugated unsaturated double bond will react with the maleic anhydride via the Alder-ene reaction. For simplicity, we show both the mono-unsaturated and the diene reacted with the maleic anhydride on the same triglyceride molecule. The extent to which this happens, if at all, will depend on the relative molar amounts of the enophile and triglycerides of the oil; the level if unsaturation and conjugation.

It is thought that the adduct (3) reacts with the hydroxyl ethyl methacrylate to form structure depicted as (4).

FIG. 2 shows the reaction of structure 4 with glycerol to form one of the species (5) of the macromonomer.

In a further aspect of the invention there is provided a polymerisable ethylenically unsaturated macromonomer made according to the process hereinbefore described The reaction of the enophile with the unsaturated bonds of the triglycerides is preferably carried out at temperatures above 100° C., more preferably from 100 to 250° C., even more preferably from 125 to 250° C., yet more preferably from 150 to 250° C. and most preferably from 180 to 250° C.

Depending on the choice of unsaturated oil, the resultant neat macromonomer can vary in appearance at room temperature from a reasonably fluid liquid to a greasy or even waxy consistency.

In a further aspect of the invention, there is provided an addition polymer derived from the macromonomer as hereinbefore described. Preferably the polymer is polymerised with other ethylenically unsaturated monomers. Examples of suitable ethylenically unsaturated monomers include (meth) acrylic acid esters, amides, and nitriles, vinyl monomers and vinyl esters.

It is preferred that the polymer comprises more than 6 wt % of the macromonomer of the invention, more preferably from 6 to 80 wt %, even more preferably from 15 to 75 wt % and most preferably from 20 to 60 wt %.

Using the nomenclature of (meth)acrylate to represent both acrylate and methacrylate, examples of suitable other acrylic acid esters and methacrylic acid esters are alkyl esters, preferably methyl (meth)acrylate, ethyl (meth)acrylate, propyl (meth)acrylate, butyl (meth)acrylate, 2-ethyl hexyl (meth) acrylate and alkoxy poly(oxyethylene) (meth)acrylate. Small amounts of methacrylic acid and/or acrylic acid may also be used. Hydroxy functional monomers such as hydroxy ethyl (meth)acrylate and hydroxy isopropyl (meth)acrylate may be included also. Examples of suitable vinyl monomers include styrene and alpha methyl styrene, vinyl propionate, vinyl butyrate, vinyl acetate and vinyl versatate. Preferably the addition polymer is derived from the esters of acrylic acid, methacrylic acid and optionally styrene and/or its derivatives. More preferably, the other monomers are styrene and 2-ethyl hexyl acrylate.

The glass transition temperature, or Tg, of the polymer comprising the macromonomer of the invention may be varied by copolymerising monomers of appropriate Tg. In this way copolymers which are hard, soft or of intermediate Tg can be made, which can produce a wide range of physical film properties such as tack (or stickiness), hardness and extensibility. Due to the long alkyl chains of the macromonomers, the Tg's will be low, comparable to butyl acrylate, lauryl acrylate and stearyl acrylate depending on the starting oil.

Preferably the Tg of the polymer is from −70 to 185° C., more preferably from −20 to 120° C. More preferably the polymer is suitable for use as a binder in coatings especially in architectural coating compositions. For such binder polymer dispersions the preferred range is from −20 to 120° C., yet more preferably from −15 to 60° C., even more preferably from −10 to 25° C. and most preferably from −10 to 10° C. as this produces a more durable paint which is better resistant to knocks and scuffs.

More preferably, the polymer is in the form of an aqueous composition and still more preferably is an aqueous dispersion of polymer microparticles. By aqueous is meant that at least 50% by weight of the carrier liquid is water, more preferably more than 75% and most preferably the carrier liquid is water.

Preferably the polymer microparticles have a mean diameter of from 0.05 to 2 microns, more preferably from 0.05 to 1.0 microns, still more preferably from 0.05 to 1.0 microns and most preferably from 0.05 to 0.3 microns.

Optionally, the microparticles are of the core-shell type having a core polymer composition different from the shell polymer composition.

The ethylenically unsaturated monomers are caused to copolymerise by heating the monomer, in a carrier liquid-preferably water, containing polymerisation initiators, preferably to a temperature of from 30° C. to 150° C., preferably from 40° C. to 80° C. More preferably the polymerisation process used is an aqueous emulsion polymerisation process. In such a case the maximum polymerisation temperature should not exceed 98° C. Even more preferably, where redox initiator combinations are used, the preferred polymerisation temperature is from 20° C. to 80° C. and most preferably from 30° C. to 70° C.

Suitable emulsion polymerisation initiators include oxidants, for example, peroxides such as tertiary butyl hydroperoxide, hydrogen peroxide and cumene hydroperoxide; persulphates such as potassium persulphate and ammonium persulphate; azo types such as 4,4' azobis (4-cyanopentanoic acid). Preferably from 0.002% by weight to 5% by weight of the initiator is used, calculated on the amount of ethylenically unsaturated monomers, more preferably from 0.05 to 2% and most preferably from 0.1 to 1%.

Reductants may be used in combination with the oxidant to form so called redox couples. This enables the polymerisation to be run at lower temperature than when relying on thermal decomposition alone. Suitable examples of such oxidants include sodium ascorbate, sodium metabisulphite and sodium formaldehyde sulphoxylate. Suitable examples of redox couples include tertiary butyl hydroperoxide with ascorbic acid or sodium ascorbate or sodium metabisulphite or sodium formaldehyde sulphoxylate; hydrogen peroxide with ascorbic acid, sodium ascorbate or sodium metabisulphite or sodium formaldehyde sulphoxylate; cumene hydroperoxide with ascorbic acid sodium ascorbate or sodium metabisulphite or sodium formaldehyde sulphoxylate. More preferred is the redox couple tertiary butyl hydroperoxide with sodium ascorbate.

Optionally, metal salts such as copper, chromium and iron salts can be added when redox pairs are used. Such metals, usually in the form of water soluble salts, for example iron(II) sulphate, are especially useful where the natural level of dissolved metals in the reaction mixture are low. This can occur when a glass-lined reactor is used or a metal chelating agent is present. The presence of the added metal salts ensures that the redox system works effectively. Preferably the level of added metal salt is kept to a minimum to avoid discolouration of the dispersion itself and any coatings derived from it. This is generally less of a problem for adhesives.

The preferred initiator system is the redox combination of tertiary butyl hydroperoxide and ascorbic acid, the latter optionally in the form of sodium ascorbate. Such redox combinations allow the polymerisation to be carried out or around ambient temperature such as from 30 to 55° C.

In a further aspect of the invention there is provided a process of producing an aqueous dispersion of polymer microparticles derived from a monomer mixture comprising the macromonomer and other ethylenically unsaturated monomers, as hereinbefore described.

Preferably the process comprises the steps of
i) making an emulsion of ethylenically unsaturated monomers comprising the macromonomer and other monomers, in aqueous medium, preferably water, containing surfactant
ii) charging from 5 to 25% by weight of the monomer emulsion to a polymerisation vessel and causing it to polymerise of to form polymer microparticles of mean particle diameter of from 0.05 to microns
iii) feeding the remaining monomer emulsion of step i) to the vessel in the presence of the microparticles of step ii) and causing it to polymerise and grow them to form the final microparticles of mean particle diameter of from 0.05 to 2.0 microns.

More preferably, the process comprises the steps of
i) making an aqueous emulsion comprising the macromonomer and no other monomer
ii) charging the emulsion to a polymerisation vessel and adding at least some of a mixture of neat comonomers to the vessel and causing the combination of comonomers and macromonomer to polymerise to polymerise to form polymer microparticles of mean particle diameter of from 0.05 to 2 microns
iii) feeding a neat mixture of the remaining comonomers to the vessel in the presence of the microparticles of step ii) and causing it to polymerise and grow them to form the final microparticles.

This has the advantage that there is no need to make an aqueous emulsion of the macromonomer and the other ethylenically unsaturated monomers thereby saving time. Furthermore, it ensures that the macromonomer of the invention is polymerised into the particles.

In a yet further aspect of the invention there is provided a coating composition comprising the addition polymer as hereinbefore described. Preferably, the coating is aqueous. More preferably the coating is an architectural paint for use on the interior and exterior surfaces of structures such as found in homes, offices and gardens. Even more preferably, the paint is of non-Newtonian rheology, even more preferably, thixotropic rheology.

The coating composition may also contain ingredients selected from the group consisting pigments, fillers, waxes, extenders, rheological modifiers, dispersants, anti-foams, plasticisers, crosslinking agents, flow aids and biocides.

Materials Used in the Examples
Sunflower oil is available from Kerfoot, The Olive House, Standard Way Industrial Estate, Fleet, Hampshire, UK.
tert-butyl hydroperoxide (t-BHP) is available from Akzo-Nobel
Disponil A4066 is available from Henkel

EXAMPLES

Examples of the invention will now be described.
MM 1
A macromonomer was made according to the following process using the ingredients specified.
Conjugation Step
450 g of Safflower Oil is placed in a 1 litre round bottomed flask fitted with mechanical stirrer, nitrogen inlet and condenser. The oil was sparged for 4 hours prior to the addition of iodine at room temperature. 2.7 g of iodine was added to the oil and the temperature raised to 250° C. and held there for 1 hour. The oil was then cooled back to room temperature ready for the next stage in the macromonomer synthesis Adduct Step
To the oil from the conjugation stage above was charged 78.6 g of maleic anhydride and the reaction temperature raised to 200° C. The mixture was held at this temperature for one hour after which time the temperature was raised to 220° C. and held for a further 4 hours. This ensured that any remaining un-reacted maleic anhydride would add to the oil via a typical Alder-ene reaction.

The adduct was then cooled back to 200° C. and 0.75 g of phenothiazine was added and allowed to dissolve for 5 minutes. After which 48.7 g of hydroxyl ethyl methacrylate was added, via a dropping funnel, over a 30 minute period. This was held at 200° C. for a further hour.

Finally, 13.98 g of glycerol was added and reacted for an hour at 200° C. after which it was allowed to cool and the resulting macromonomer was stored ready for use.
Latex 1
The macromonomer was converted into a polymer latex according to the following process and using the ingredients listed.
Latex Example (Latex 1)
A latex was made using the following ingredients and procedure

|  | g | wt % |
| --- | --- | --- |
| Initiator |  |  |
| t-BHP/1 | 5.48 | 0.498 |
| Monomer Pre-emulsion |  |  |
| MM 1 | 171.73 | 15.612 |
| Styrene | 260.35 | 23.668 |
| 2-ethyl hexyl acrylate | 83.12 | 7.556 |
| Ammonia (25% solution) | 8.02 | 0.729 |
| Demin water/1 | 444.42 | 40.402 |
| Disponil A4066 | 43.24 | 3.931 |
| Reductant Solution |  |  |
| Demin water/2 | 77.80 | 7.073 |
| Sodium ascorbate | 3.10 | 0.282 |
| t-BHP/2 | 2.74 | 0.249 |

Prepare 523.22 g of Monomer Pre-emulsion by mixing the indicated weights of macromonomer MM 1, styrene, 2-EHA and adding the ammonia under gentle stirring for about 10 minutes, adding the ammonia dropwise. Add this monomer mixture to a solution of 444.42 g of Demin/1 and 43.24 g Disponil A4066 under high shear mixing conditions using a Silverson homogeniser to form an emulsion of monomer in water until the mean droplet size is about 150 nm and there are no monomer droplets greater than 2000 nm. This will require about 20 minutes.

Prepare the reductant solution by dissolving the sodium ascorbate in water

To a 2l parallel sided vessel fitted with a propeller stirrer, condenser and a nitrogen blanket, add 350.00 g of the Monomer Pre-emulsion and raise the temperature to 50° C. and add t-BHP/1. After 5 minutes at this temperature add 20.23 g of the reductant solution. Allow the batch to exotherm for 5 minutes and then feed the remainder of the Monomer Pre-emulsion (MPE) linearly over 60 minutes whilst concurrently feeding 26.97 g of the Reductant solution, linearly. Maintain at 50° C. for a further 15 minutes and then add 6.74 g of the Reductant solution and hold for a further 15 minutes. Add t-BHP/2 and maintain temperature for a further 5 minutes after which time add the remaining Reductant solution, 26.97 g linearly over 30 minutes. Maintain at 50° C. for 15 minutes and then cool and filter through 80 mesh nylon.

There was very little build-up on the reactor walls or the stirrer and the latex was bit free.

The latex constants were
pH: 7.2 subsequently adjusted to 8.5
weight solids: 50.0%
Mean particle size was 145 nm measured on a Malvern Mastersizer
Effect of Iodine Level The effect of iodine level on conjugation was estimated by repeating the conjugation step in MM 1 but replacing the 2.7 g of iodine with 1.35 g (0.3 wt %) and 1.8 g (0.4 wt %) of iodine. The composition of the triglycerides in the oil was assessed using Nuclear Magnetic Resonance (NMR) and Matrix Assisted Laser Desorption/Ionisation (MALDI).

As the amount of iodine increases so does the amount of conjugation as indicated by the decrease in the non-conjugated linoleic acid and the increase in the conjugated linoleic acid.

Table 1 shows the increase in conjugated linoleic acid as the iodine level increases.

TABLE 1

| % Iodine* | % Total Unsat | % non-conjugated linoleic acid | % conjugated linoleic acid | % Dimer |
|---|---|---|---|---|
| 0 | 92.6 | 75.6 | 0 | 0 |
| 0.3 | 89 | 37.7 | 27.8 | 12.5 |
| 0.4 | 81.2 | 16.8 | 34.8 | 26.4 |
| 0.6 | 78 | 1.3 | 36.6 | 39.8 |

Temperature was 250° C.

The dimer is formed by a 'bodying' type reaction.
Effect of Temperature on Conjugation The conjugation step of MM 1 was repeated and the temperature varied from 125 to 225° C.

Table 2 shows the effect of temperature on the conjugation.

TABLE 2

| Temperature ° C. | % Total Unsat | % non-conjugated linoleic acid | % conjugated linoleic acid | % Dimer |
|---|---|---|---|---|
| 125 | 92.6 | 63.4 | 21.2 | 0 |
| 150 | 92.0 | 37.6 | 37.4 | 0.6 |
| 162.5 | 92.0 | 18.8 | 52.1 | 4.7 |
| 175 | 92.0 | 10.1 | 53.3 | 14.6 |
| 200 | 88.8 | 7.2 | 48.3 | 22.5 |
| 225 | 83.8 | 3 | 42.5 | 32.5 |
| 250 | 78.0 | 1.3 | 36.6 | 39.8 |

The iodine level was 0.6 wt %

As the temperature increases more conjugated linoleic acid is formed
Effect of Conjugation Temperature on Yellowing The conjugated safflower oils of Table 2 were converted to macromonomers using the ingredients and process of MM 1. This produced seven macromonomers derived from oils conjugated at the temperatures indicated in Table 2. These were copolymerised with other ethylenically unsaturated monomers according to the recipe and process of Latex 1 other than the macromonomer MM 1 was replaced by the macromonomers derived from the conjugated oils of Table 2.

Each latex was drawn down on a white substrate and allowed to dry (film thickness about 75 microns). The yellowness was measured and compared to a styrene/ethyl hexyl acrylate copolymer latex.

Table 3 shows the yellowing measured after exposure under different conditions,

TABLE 3

| Temperature | dE 24 hrs at RT | dE 7 days at room temp. on a windowsill | dE 7 days at 40° C. in the Dark |
|---|---|---|---|
| 125° C. | 0.87 | 4.74 | 2.27 |
| 150° C. | 0.59 | 3.89 | 1.28 |
| 175° C. | 0.49 | 2.54 | 1.19 |
| 200° C. | 0.43 | 1.37 | 0.74 |
| 225° C. | 0.46 | 1.45 | 1.07 |
| 250° C. | 0.60 | 1.54 | 1.11 |

Yellowing was measured using a Zeiss Spectrometer (type MCS551VIS, spectral range 360-780 nm) fibre optically coupled to an integrating sphere.

Each value in the table is positive, indicating that the macromonomer containing latices are more yellow than the St/EHA latex.

The latices derived from macromonomers which were conjugated at 200 to 250° C. are, on the whole less yellow to start with and yellow much less on aging.

The invention claimed is:

1. A process for making a polymerisable ethylenically unsaturated macromonomer from unsaturated non-mineral oil, the oil being a mixture of triglycerides, some of which comprise at least one fatty acid having at least two non-conjugated unsaturated bonds at least one of which is ethylenically unsaturated, the process comprising the steps of
   i) conjugating the non-conjugated unsaturated bonds;
   ii) reacting the reaction product of step i) with an enophile having an acid, ester or anhydride moiety to form an adducts;
   iii) reacting the adduct with an ethylenically unsaturated monomer having a moiety reactive with the acid, ester or anhydride moiety of the enophile to form an intermediate;
   iv) reacting the intermediate of step iii) with a chain extender having at least two moieties reactive with the acid, ester or anhydride moiety of the enophile to form the macromonomer;
wherein the oil has an iodine value of from 110 to 180g of iodine per 100g of oil.

2. The process according to claim 1 wherein the non-conjugated unsaturated bonds are all ethylenically unsaturated.

3. The process according to claim 1 wherein the conjugation step of step i) is carried out by reacting the oil with from 0.1 to 0.8 wt % of iodine, calculated on the weight of oil, at a temperature between 125 and 270° C.

4. The process according to claim 3 wherein the amount of iodine in step i) is from 0.2 to 0.8 wt %.

5. The process according to claim 1 wherein the temperature in step i) is from 150 to 270° C.

6. The process according to claim 1 wherein the oil is safflower oil.

7. The process according to claim 1 wherein the enophile is selected from the group consisting of maleic anhydride, itaconic anhydride, fumaric acid, acrylic acid and maleate esters.

8. The process according to claim 1 wherein the ethylenically unsaturated monomer reactive with the acid, ester or anhydride of the enophile is selected from the group consisting of hydroxyl ethyl (meth)acrylate, hydroxyl propyl (meth) acrylate, hydroxyl iso propyl methacrylate, hydroxyl butyl methacrylate, allyl alcohol, glycerol methacrylate, glycidyl (meth)acrylate, allyl amine, and tert-butyl aminoethyl methacrylate.

9. The process according to claim 1 wherein the chain extender is glycerol.

10. The process according to claim 1 wherein the molar ratio of oil:enophile:unsaturated monomer:chain extender is 1:1.5:0.75:0.30.

11. The process according to claim 1 wherein the macromonomer has a weight average molecular weight, Mw, of from 1000 to 50000 Daltons.

12. An ethylenically unsaturated macromonomer made according to the process of claim 1.

13. An addition polymer derived from an ethylenically unsaturated monomer composition comprising the unsaturated macromonomer of claim 12.

14. The addition polymer according to claim 13 wherein the polymer is in the form of an aqueous dispersion of polymer microparticles.

15. The addition polymer according to claim 14 wherein the microparticles have a mean average diameter of from 0.05 microns to 2.00 microns.

16. The addition polymer according to claim 14 wherein the polymer has a Tg of from −20 to 120° C.

17. A coating composition comprising the addition polymer of claim 15.

18. The coating composition according to claim 17, further comprising an ingredient selected from the group consisting of pigments, fillers, waxes, extenders, rheological modifiers, dispersants, anti-foams, tackifiers, plasticisers, flow aids and biocides.

19. The process according to claim 3 wherein the oil is safflower oil.

20. The process according to claim 8 wherein the molar ratio of oil:enophile:unsaturated monomer:chain extender is 1:1.5:0.75:0.30.

* * * * *